000000000000000000000

United States Patent [19]

Clark

[11] Patent Number: 4,876,250
[45] Date of Patent: Oct. 24, 1989

[54] METHODS FOR CONTROLLING OCULAR HYPERTENSION WITH ANGIOSTATIC STEROIDS

[75] Inventor: Abbot F. Clark, Arlington, Tex.

[73] Assignee: Alcon Laboratories, Inc., Fort Worth, Tex.

[21] Appl. No.: 264,918

[22] Filed: Oct. 31, 1988

[51] Int. Cl.$^4$ .................. A61K 31/56; A61K 31/58
[52] U.S. Cl. .................................. 514/179; 514/172; 514/173; 514/176; 514/180; 514/182
[58] Field of Search ............... 514/179, 172, 182, 173, 514/176, 180

[56] References Cited

FOREIGN PATENT DOCUMENTS 250088 5/1987 European Pat. Off. .
WO86/02189 10/1986 PCT Int'l Appl. .

OTHER PUBLICATIONS

Knepper et al., *Exp. Eye Res.*, 27,567–575 (1978) "Intraocular Pressure & Glycosaminoglycan Distribution in the Rabbit Eye: Effect of Age and Dexamethasone".
Hester et al., *J. Ocular Pharmacology*, vol. 3, No. 3, 185–189 (1987) "Steroid–Induced Ocular Hypertension in the Rabbit; A Model Using Subconjunctival Injections".
Crum et al., *Science*, vol. 230, 13/5–1378 (Dec., 1985) "A New Class of Steroids Inhibits Angiogenesis in the Presence of Heparin or a Heparin Fragment".
Ingber et al., *Endocrinology*, vol. 119, No. 4, 1768–1775 (1986) "A Possible Mechanism for Inhibition of Angiogenesis by Angiostatic Steroids:Induction of Capillary Basement Membrane Dissolution".
Southren et al., *Invest. Uphth. & Vis. Science*, vol. 28, 901–903 (1978) "Intraocular Hypotensive Effect of a Topically Applied Cortisol Metabolite:$3\alpha,5\beta$-Tetrahydrocortisol".
Folkman et al., *Ann. Surg.*, vol. 206, No. 3,374–382 (1987) "Angiostatic Steroids".
Knepper et al., *Pediatric Neuroscience*, 12:240–251 (1985–86)"Glycosaminoglycans and Outflow Pathways of the Eye and Brain".
Johnson et al., *Mayo Clin. Proc.*, 61:59–67 (1986 "Glaucoma: An Overview".
Rohen, Johannes W., *Ophthalmology*, vol. 90, No. 7,758–764 (1983) "Why is Intraocular Pressure Elevated in Chronic Simple Glaucoma?".
Knepper et al., *Invest. Ophth & Vis. Science*, vol. 26, 1093–1100 (Aug., 1985) "Effect of Dexamethasone, Progesterone, and Testosterone on IOP & GAGs in the Rabbit Eye".
Southren et al., *Invest. Ophth & Vis. Science*, vol. 26, 393–395 (Mar., 1985) "$5\beta$–Dihydrocortisol: Possible Mediator of the Ocular Hypertension in Glaucoma".

*Primary Examiner*—Douglas W. Robinson
*Assistant Examiner*—Joseph A. Lipovsky
*Attorney, Agent, or Firm*—James Arno; Gregg Brown; Sally Stewart

[57] ABSTRACT

Angiostatic steroids for use in controlling ocular hypertension are disclosed. Pharmaceutical composition of the angiostatic steroids and methods for their use in treating ocular hypertension, including controlling the ocular hypertension associated with primary open angle glaucoma, are disclosed.

6 Claims, 1 Drawing Sheet

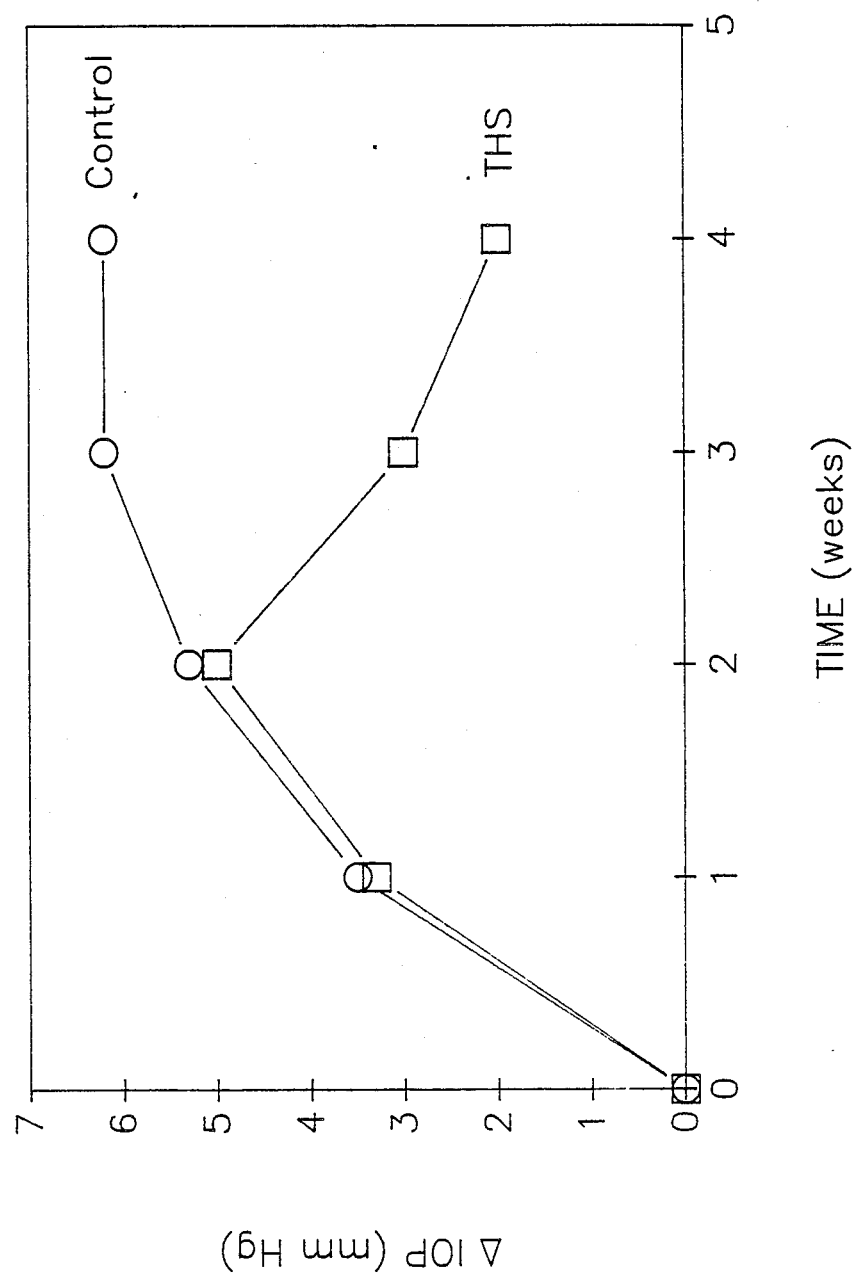

METHODS FOR CONTROLLING OCULAR HYPERTENSION WITH ANGIOSTATIC STEROIDS

BACKGROUND OF THE INVENTION

1. Field of the Invention

This invention relates to methods and compositions for controlling ocular hypertension. Specifically, the invention is directed to pharmaceutical compositions comprising angiostatic steroids and methods of treatment comprising administering these compositions to treat ocular hypertension, including controlling ocular hypertension associated with primary open angle glaucoma.

2. Description of Related Art

Steroids functioning to inhibit angiogenesis in the presence of heparin or specific heparin fragments are disclosed in Crum, et al., *A New Class of Steroids Inhibits Angiogenesis in the Presence of Heparin or a Heparin Fragment*, Science, Vol. 230, pp. 1375–1378 (Dec. 20, 1985). The authors refer to such steroids as "angiostatic" steroids. Included within the new class of steroids found to be angiostatic are the dihydro and tetrahydro metabolites of cortisol and cortexolone. In a follow-up study directed to testing a hypothesis as to the mechanism by which the steroids inhibit angiogenesis, it was shown that heparin/angiostatic steroid compositions cause dissolution of the basement membrane scaffolding to which anchorage dependent endothelia are attached resulting in capillary involution; see, Ingber, et al., *A Possible Mechanism for Inhibition of Angiogenesis by Angiostatic Steroids: Induction of Capillary Basement Membrane Dissolution*, Endocrinology 119, pp. 1768–1775 (1986).

A group of tetrahydro steroids useful in inhibiting angiogenesis is disclosed in International Patent Application No. PCT/US86/02189, Aristoff, et al., (The UpJohn Company). The compounds are disclosed for use in treating head trauma, spinal trauma, septic or traumatic shock, stroke and hemorrhage shock. In addition, the patent application discusses the utility of these compounds in embryo implantation and in the treatment of cancer, arthritis and arteriosclerosis. The compounds are not disclosed for ophthalmic use.

Tetrahydrocortisol (THF) has been disclosed for its use in lowering the intraocular pressure (IOP) of rabbits made hypertensive with dexamethasone alone, or with dexamethasone/5-beta-dihydrocortisol; see Southren, et al., *Intraocular Hypertensive Effect of a Topically Applied Cortisol Metabolite: 3-alpha, 5-beta-tetrahydrocortisol*, Investigative Ophthalmology and Visual Science, Vol. 28 (May, 1987). The authors suggest THF may be useful as an antiglaucoma agent. In European Patent Application, Publication Number 250,088, Southren, et al., pharmaceutical compositions containing THF and a method for using these compositions to control intraocular pressure are disclosed. THF has been disclosed as an angiostatic steroid in Folkman, et al., *Angiostatic Steroids*, Ann. Surg., Vol. 206, No. 3 (1987) wherein it is suggested angiostatic steroids may have potential use for diseases dominated by abnormal neovascularization, including diabetic retinopathy, neovascular glaucoma and retrolental fibroplasia.

BRIEF DESCRIPTION OF THE DRAWING

The sole FIGURE of drawing is a graph which illustrates the IOP lowering effectiveness of tetrahydrocortexolone (THS) on rabbits with steroid induced ocular hypertension.

SUMMARY OF THE INVENTION

This invention is directed to compositions comprising angiostatic steroids and steroid metabolites useful for controlling ocular hypertension. The compositions are particularly useful in the treatment of primary open angle glaucoma.

In addition the invention encompasses methods for controlling ocular hypertension through the topical administration of the compositions disclosed herein.

DETAILED DESCRIPTION OF PREFERRED EMBODIMENTS

The development of blood vessels for the purpose of sustaining viable tissue is known as angiogenesis. Agents which inhibit angiogenesis are known by a variety of terms such as angiostatic, angiolytic or angiotropic agents. For purposes this specification, the term "angiostatic agent" means compounds which can be used to inhibit angiogenesis.

The angiostatic agents of the present invention are steroids or steroid metabolites. For purposes herein, the term "angiostatic steroids" means steroids and steroid metabolites which inhibit angiogenesis. The present invention is based on the finding that angiostatic steroids can be used for the control of ocular hypertension. In particular, the agents can be used for the treatment of primary open angle glaucoma.

Agents which can be used according to the present invention comprises angiostatic steroids. Angiostatic steroids which can be used will typically comprise the angiostatic steroids disclosed in PCT/US86/02189 which have the following formula:

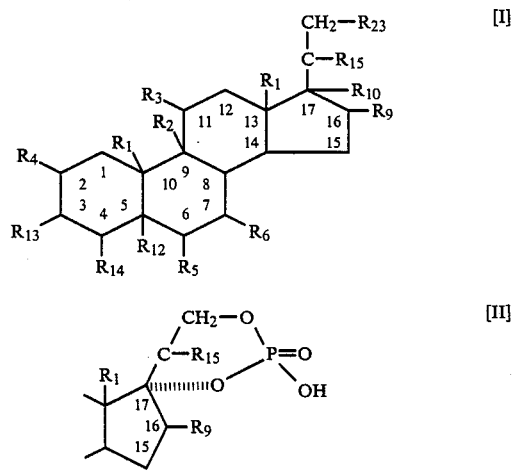

wherein
$R_1$ is $\beta$-$CH_3$ or $\beta$-$CH_2H_5$;
$R_2$ is H or —Cl;
$R_3$ is H, =O, —OH, —O—alkyl($C_1$-$C_{12}$), —OC(=O)alkyl($C_1$-$C_{12}$), —OC(=O)ARYL, —OC(=O)N(R)$_2$ or $\alpha$—OC(=O)OR$_7$, wherein ARYL is furyl, thienyl, pyrrolyl, or pyridyl and each of said moieties is optionally substituted with one or two ($C_1$-$C_4$)alkyl groups, or ARYL is —(CH$_2$)$_f$phenyl wherein f is 0 to 2 and the phenyl ring is optionally substituted with 1 to 3 groups selected from chlorine, fluorine, bromine, alkyl($C_1$-$C_3$), alkoxy(C-

$1$-$C_3$), thioalkoxy-($C_1$-$C_3$), $Cl_3C$—, $F_3C$—, —$NH_2$ and —$NHCOCH_3$ and R is hydrogen, alkyl ($C_1$-$C_4$), or phenyl and each R can be the same or different, and $R_7$ is ARYL as herein defined, or alkyl($C_1$-$C_{12}$); or wherein
  $R_2$ and $R_3$ taken together are oxygen (—O—) bridging positions C-9 and C-11; or
wherein
  $R_2$ and $R_3$ taken together form a double bond between positions C-9 and C-11; or
  $R_2$ is $\alpha$—F and $R_3$ is $\beta$—OH; or
  $R_2$ is $\alpha$—Cl and $R_3$ is $\beta$—Cl; and
  $R_4$ is H, $CH_3$, Cl or F;
  $R_5$ is H, OH, F, Cl, Br, $CH_3$, phenyl, vinyl or allyl;
  $R_6$ is H or $CH_3$;
  $R_9$ is H, OH, $CH_3$, F or =$CH_2$;
  $R_{10}$ is H, OH, $CH_3$ or $R_{10}$ forms a second bond between positions C-16 and C-17;
  $R_{12}$ is —H or forms a double bond with $R_{14}$;
  $R_{13}$ is H, —OH, =O, —O—P(O)(OH)$_2$, or —O—C(=O)—(CH$_2$)$_t$COOH where t is an integer from 2 to 6;
  $R_{14}$ is H or forms a double bond with $R_{12}$;
  $R_{15}$ is =O or —OH; and
  $R_{23}$ with $R_{10}$ forms a cyclic phosphate as depicted by Formula II;
wherein
  $R_9$ and $R_{15}$ have the meaning defined above; or
  wherein $R_{23}$ is —OH, O—C(=O)—$R_{11}$, —OP-(O)—(OH)$_2$, or —O—C(=O)— (CH$_2$)$_t$COOH wherein t is an integer from 2 to 6; and $R_{11}$ is —Y—(CH$_2$)$_n$—X—(CH$_2$)$_m$—SO$_3$H, —Y'—(CH$_2$)$_p$—X'—(CH$_2$)$_q$—NR$_{16}$R$_{17}$ or —Z(CH$_2$)$_r$Q, wherein Y is a bond or —O—; Y' is a bond, —O—, or —S—; each of X and X' is a bond, —CON($R_{18}$)—, —N($R_{18}$)CO—, —O—, —S—, —S(O)—, or —S-($O_2$)—; $R_{18}$ is hydrogen or alkyl ($C_1$-$C_4$); each of $R_{16}$ and $R_{17}$ is a lower alkyl group of from 1 to 4 carbon atoms optionally substituted with one hydroxyl or $R_{16}$ and $R_{17}$ taken together with the nitrogen atom to which each is attached forms a monocyclic heterocyclic selected from pyrrolidino, piperidino, morpholino, thiomorpholino, piperazino or N(lower)alkyl-piperazino wherein alkyl has from 1 to 4 carbon atoms; n is an integer of from 4 to 9; m is an integer of from 1 to 5; p is an integer of from 2 to 9; q is an integer of from 1 to 5;
  Z is a bond or —O—; r is an integer of from 2 to 9; and Q is one of the following:
  (1) —$R_{19}$—CH$_2$COOH wherein $R_{19}$ is —S—, —S-(O)—, —S(O)$_2$—, —SO$_2$N($R_{20}$)—, or N($R_{20}$)SO$_2$—; and $R_{20}$ is hydrogen or lower alkyl-($C_1$-$C_4$); with the proviso that the total number of carbon atoms in $R_{20}$ and (CH$_2$)$_r$ is not greater than 10; or
  (2) —CO—COOH; or
  (3) CON($R_{21}$)CH($R_{22}$)COOH wherein $R_{21}$ is H and $R_{22}$ is H, $CH_3$, —CH$_2$COOH, —CH$_2$CH$_2$COOH, —CH$_2$OH, —CH$_2$SH, —CH$_2$CH$_2$SCH$_3$, or —CH$_2$-Ph—OH wherein Ph—OH is p-hydroxyphenyl; or $R_{21}$ is $CH_3$ and $R_{22}$ is H; or $R_{21}$ and $R_{22}$ taken together are —CH$_2$CH$_2$CH$_2$—; or —N($R_{21}$)CH($R_{22}$)COOH taken together is —NHCH$_2$CONHCH$_2$COOH; and pharmaceutically acceptable salts thereof; with the proviso that except for the compound wherein $R_1$ is —$CH_3$, $R_2$ and $R_3$ taken together from a double bond between positions 9 and 11, $R_4$ and $R_6$ are hydrogen, $R_{12}$ and $R_{14}$ taken together form a double bond between positions 4 and 5, $R_5$ is $\alpha$—F, $R_9$ is $\beta$—$CH_3$, $R_{10}$ is $\alpha$—OH, $R_{13}$ and $R_{15}$ are =O and $R_{23}$ is —OP(O)—(OH)$_2$, $R_{13}$ is =O only when $R_{23}$ with $R_{10}$ forms the above described cyclic phosphate.

Excepted from the compounds of Formula I is the compound 3,11$\beta$, 17$\alpha$, 21-tetrahydroxy-5 pregnane-20-one (the 3-alpha, 5-beta; 3-alpha, 5-alpha; 3-beta, 5-alpha; and 3-beta, 5-beta isomers of tetrahydrocortisol) wherein:
  $R_{15}$ is =O; $R_{10}$ is $\alpha$ OH;
  $R_1$ is $CH_3$; $R_3$ is $\beta$ OH; $R_2$ is H; $R_4$ is H; $R_{13}$ is $\alpha$ or $\beta$ OH; $R_{14}$ is H;
  $R_{12}$ is $\alpha$ or $\beta$ H; $R_5$ is H; $R_6$ is H; $R_9$ is H and $R_{23}$ is OH.

Unless specified otherwise, all substituent groups attached to the cyclopenta phenanthrene moiety of Formula I may be in either the alpha or beta position. Additionally, the above structures include all pharmaceutically acceptable salts of the angiostatic steroids.

Preferred angiostatic steroids are:

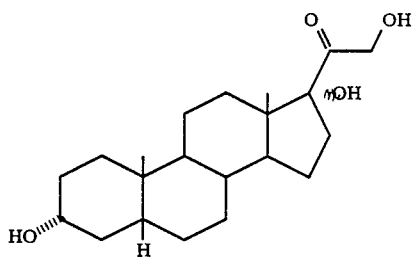

Tetrahydrocortexolone (THS) and its pharmaceutically acceptable salts;

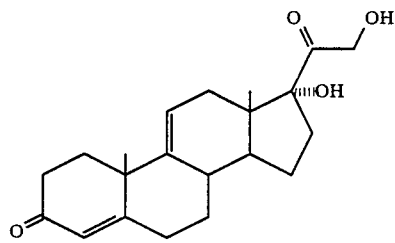

4,9(11)-pregnadien 17$\alpha$,21-diol-3,20-dione and its pharmaceutically acceptable salts;

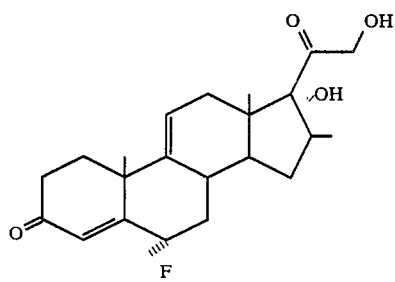

6$\alpha$-fluoro-17$\alpha$,21-dihydroxy-16$\beta$-methyl-pregna-4,9(11)-diene-3,20-dione and its pharmaceutically acceptable salts.

Without intending to be bound by any theory, it is believed that the angiostatic steroids of the type described above act to control intraocular pressure by inhibiting the accumulation or stimulating the dissolution of amorphous extracellular material in the trabecular meshwork of the eye. The presence of this amorphous extracellular material alters the integrity of the healthy trabecular meshwork and is a symptom associated with primary open angle glaucoma (POAG). It is not well understood why this amorphous extracellular material builds up in the trabecular meshwork of persons suffering fro POAG. However, it has been found that the amorphous extracellular material is generally composed of glycosaminoglycans (GAGs) and basement membrane material; see, *Ophthalmology*, Vol. 90, No. 7 (July 1983); *Mayo Clin. Proc*, Vol. 61, pp. 59–67 (January 1986); and *Pediat. Neurosci.* Vol. 12, pp. 240–251 (1985–86). When these materials build up in the trabecular meshwork, the aqueous humor, normally present in the anterior chamber of the eye, cannot leave this chamber through its normal route (the trabecular meshwork) at its normal rate. Therefore, a normal volume of aqueous humor is produced by the ciliary processes of the eye and introduced into the anterior chamber, but its exit through the trabecular meshwork is abnormally slow. This results in a buildup of pressure in the eye, ocular hypertension, which can translate into pressure on the optic nerve. The ocular hypertension so generated can lead to blindness due to damage to the optic nerve.

Many methods for treating primary open angle glaucoma and ocular hypertension concentrate on blocking production of aqueous humor by the eye. However, aqueous humor is the fundamental source of nourishment for the tissues of the eye, particularly the cornea and lens which are not sustained by blood supply. Therefore, it is not desirable to deprive these tissues of the necessary irrigation and nutrition provided by the aqueous humor. It is desirable to strive for normal exit of the aqueous humor by maintaining the normal integrity of the trabecular meshwork. This is accomplished according to the present invention by the administration of angiostatic steroids.

It is believed that the angiostatic steroids disclosed herein function in the trabecular meshwork in a similar manner as shown by Ingber, et al., wherein it was shown that angiostatic steroids caused dissolution of the basement membrane scaffolding using a chick embryo neovascularization model; *Endocrinology*, 119, pp. 1768–1775 (1986). It is believed that the angiostatic steroids of the present invention prevent the accumulation, or promote the dissolution of, amorphous extracellular materials in the trabecular meshwork by inhibiting the formation of basement membrane materials and glycosaminoglycans. Thus, by preventing the development of these materials or promoting their dissolution, the normal integrity of the trabecular meshwork is retained and aqueous humor may flow through the trabecular meshwork at normal rates. As a result, the intraocular pressure of the eye is controlled.

The angiostatic steroids of the present invention may be incorporated in various formulations for delivery to the eye. For example, topical formulations can be used and can include ophthalmologically acceptable preservatives, surfactants, viscosity enhancers, buffers, sodium chloride and water to form aqueous sterile ophthalmic solutions and suspensions. In order to prepare sterile ophthalmic ointment formulations, an angiostatic steroid is combined with a preservative in an appropriate vehicle, such as mineral oil, liquid lanolin or white petrolatum. Sterile ophthalmic gel formulations comprising the angiostatic steroids of the present invention can be prepared by suspending an angiostatic steroid in a hydrophilic base prepared from a combination of, for example, Carbopol-940 (a carboxyvinyl polymer available from the B. F. Goodrich Company) according to published formulations for analogous ophthalmic preparations. Preservatives and tonicity agents may also be incorporated in such gel formulations.

The specific type of formulations selected will depend on various factors, such as the angiostatic steroid or its salt being used, and the dosage frequency. Topical ophthalmic aqueous solutions, suspensions, ointments and gels are the preferred dosage forms. The angiostatic steroid will normally be contained in these formulations in an amount of from about 0.005 to about 2.0 weight percent (wt.%). Preferable concentrations range from about 0.05 to about 1.0 wt.%. Thus, for topical administration, these formulations are delivered to the surface of the eye one to four times per day, depending upon the routine discretion of the skilled clinician.

EXAMPLE 1

The formulation set out below illustrates a topical ophthalmic composition which can be used according to the present invention.

| Component | Wt. % |
| --- | --- |
| THS | 0.005 to 2.0 |
| Tyloxapol | 0.01 to 0.05 |
| Benzalkonium Chloride | 0.01 |
| Sodium Chloride | 0.8 |
| Edetate Disodium | 0.01 |
| NaOH/HCl | q.s. pH 7.4 |
| Purified Water | q.s. 100 ml |

EXAMPLE 2

It has been shown that young rabbits can be made ocular hypertensive by topical administration of a potent glucocorticoid; see, *Experimental Eye Research*, 27:567 (1978); *Investigative Ophthalmology and Visual Science*, 26:1093 (1985); or by a combination of glucocorticoid with the cortisol metabolite dihydrocortisol; see, *Investigative Ophthalmology and Visual Science*, Vol. 26 (March, 1985). Ocular injections of glucocorticoids have also been shown to induce ocular hypertension in rabbits; see, *J. Ocular Pharmacology*, 3:185–189 (1987). This ocular injection rabbit model was used to test the effect of the angiostatic steroid, tetrahydrocortexolone (THS), on ocular hypertension. New Zealand red rabbits weighing approximately 1 kg. were given weeklgy Subtenon's injections of dexamethasone-acetate and 5β-dihydrocortisol in two quadrants of each eye (approximately 1 mg dexamethasone-acetate and 5β-dihydrocortisol/kg body wt./week). Intraocular pressures were taken weekly with an Alcon application pneumotonometer. Each group contained 4–5 animals. After two weeks of steroid treatment, IOP was elevated by 5 mm Hg. Half the animals then received Subtenon's injections of THS (approximately 3 mg/kg body wt./week) in addition to the 1 mg/kg body wt./week of dexamethasone/5β-dihydrocortisol. The other half continued to receive dexamethasone/5β-dihydrocortisol injections of approximately 1 mg/kg body wt./week.

FIG. I illustrates the IOP lowering effect of the angiostatic steroid, THS, in the rabbits with glucocorticoid induced ocular hypertension described above. The plots show average IOP data of the animals through a four week period. After four weeks, the group which was given THS in addition to dexamethasone/5β-dihydrocortisol (—□—□—) exhibited an approximately 4 mm Hg drop in IOP compared to the control group (—O—O—) which received dexamethasone acetate/5β-dihydrocortisol. These results indicate that the angiostatic steroid, THS, is effective in lowering intraocular pressure in rabbits with steroid induced ocular hypertension.

I claim:

1. A method for controlling ocular hypertension associated with primary open angle glaucoma, which comprises:

administering a therapeutically effective amount of an angiostatic steroid having the formula:

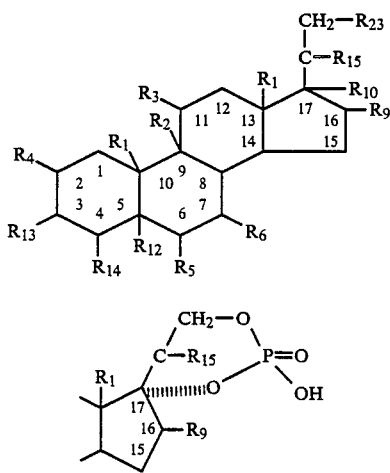

wherein $R_1$ is β—$CH_3$ or β—$CH_2H_5$;

$R_2$ is H or —Cl;

$R_3$ is H, =O, —OH, —O—alkyl($C_1$-$C_{12}$), —OC(=O)alkyl($C_1$-$C_{12}$), —OC(=O)ARYL, —OC(=O)N(R)$_2$ or α—OC(=O)OR$_7$, wherein ARYL is furyl, thienyl, pyrrolyl, or pyridyl and each of said moieties is optionally substituted with one or two ($C_1$-$C_4$)alkyl groups, or ARYL is —($CH_2$)$_f$-phenyl wherein f is 0 to 2 and the phenyl ring is optionally substituted with 1 to 3 groups selected from chlorine, fluorine, bromine, alkyl($C_1$-$C_3$), alkoxy($C_1$-$C_3$), thioalkoxy-($C_1$-$C_3$), $Cl_3C$—, $F_3C$—, —$NH_2$ and —$NHCOCH_3$ and R is hydrogen, alkyl ($C_1$-$C_4$), or phenyl and each R can be the same or different, and $R_7$ is ARYL as herein defined, or alkyl($C_1$-$C_{12}$); or wherein $R_2$ and $R_3$ taken together are oxygen (—O—) bridging positions C-9 and C-11; or wherein $R_2$ and $R_3$ taken together form a double bond between positions C-9 and C-11; or $R_2$ is α—F and $R_3$ is β—OH; or $R_2$ is α—Cl and $R_3$ is β—Cl; and $R_4$ is H; $CH_3$, Cl or F;

$R_5$ is H, OH, F, Cl, Br, $CH_3$, phenyl, vinyl or allyl;

$R_6$ is H or $CH_3$; $R_9$ is H, OH, $CH_3$, F or =$CH_2$;

$R_{10}$ is H, OH, $CH_3$ or $R_{10}$ forms a second bond between positions C-16 and C-17;

$R_{12}$ is —H or forms a double bond with $R_{14}$;

$R_{13}$ is H, —OH, =O, —O—P(O)(OH)$_2$, or —O—C(=O)—($CH_2$)$_t$COOH where t is an integer from 2 to 6;

$R_{14}$ is H or forms a double bond with $R_{12}$;

$R_{15}$ is =O or —OH; and $R_{23}$ with $R_{10}$ forms a cyclic phosphate as depicted by Formula II;

wherein $R_9$ and $R_{15}$ have the meaning defined above; or wherein $R_{23}$ is —OH, O—C(=O)—$R_{11}$, —OP(O)—(OH)$_2$, or —O—C(=O)—($CH_2$)$_t$COOH wherein t is an integer from 2 to 6; and $R_{11}$ is —Y—($CH_2$)$_n$—X—($CH_2$)$_m$—$SO_3H$, —Y'—($CH_2$)p—X'—($CH_2$)$_q$—$NR_{16}R_{17}$ or —Z($CH_2$)$_r$Q, wherein Y is a bond or —O—; Y' is a bond, —O—, or —S—; each of X and X' is a bond, —CON($R_{18}$)—, —N($R_{18}$)CO—, —O—, —S—, —S(O)—, or —S(O$_2$)—; $R_{18}$ is hydrogen or alkyl ($C_1$-$C_4$); each of $R_{16}$ and $R_{17}$ is a lower alkyl group of from 1 to 4 carbon atoms optionally substituted with one hydroxyl or $R_{16}$ and $R_{17}$ taken together with the nitrogen atom to which each is attached forms a monocyclic heterocyclic selected from pyrrolidino, piperidino, morpholino, thiomorpholino, piperazino or N(lower)alkyl-piperazino wherein alkyl has from 1 to 4 carbon atoms; n is an integer of from 4 to 9; m is an integer of from 1 to 5; p is an integer of from 2 to 9; q is an integer of from 1 to 5;

Z is a bond or —O—; r is an integer of from 2 to 9; and Q is one of the following:

(1) —$R_{19}$—$CH_2COOH$ wherein $R_{19}$ is —S—, —S(O)—, —S(O)$_2$—, —$SO_2N(R_{20})$—, or $N(R_{20})SO_2$—; and $R_{20}$ is hydrogen or lower alkyl—($C_1$-$C_4$); with the proviso that the total number of carbon atoms in $R_{20}$ and ($CH_2$)$_r$ is not greater than 10; or (2) —CO—COOH; or (3) CON($R_{21}$)CH($R_{22}$)COOH wherein $R_{21}$ is H and $R_{22}$ is H, $CH_3$, —$CH_2COOH$, —$CH_2CH_2COOH$, —$CH_2OH$, —$CH_2SH$, —$CH_2CH_2SCH_3$, or —$CH_2Ph$—OH (wherein Ph—OH is p-hydroxyphenyl); or $R_{21}$ is $CH_3$ and $R_{22}$ is H; or $R_{21}$ and $R_{22}$ taken together are —$CH_2CH_2CH_2$—; or —N($R_{21}$)CH($R_{22}$)COOH taken together is —$NHCH_2CONHCH_2COOH$; and pharmaceutically acceptable salts thereof; with the proviso that except for the compound wherein $R_1$ is —$CH_3$, $R_2$ and $R_3$ taken together form a double bond between positions 9 and 11, $R_4$ and $R_6$ are hydrogen, $R_{12}$ and $R_{14}$ taken together form a double bond between positions 4 and 5, $R_5$ is α—F, $R_9$ is β—$CH_3$, $R_{10}$ is α—OH, $R_{13}$ and $R_{15}$ are =O and $R_{23}$ is —OP(O)—(OH)$_2$, $R_{13}$ is =O only when $R_{23}$ with $R_{10}$ forms the above described cyclic phosphate and except the compounds wherein $R_{15}$ is =O;

$R_{10}$ is α OH; $R_1$ is $CH_3$; $R_3$ is β OH; $R_2$ is H; $R_4$ is H; $R_{13}$ is α or β OH; $R_{14}$ is H;

$R_{12}$ is α or β H; $R_5$ is H; $R_6$ is H; $R_9$ is H and $R_{23}$ is OH.

2. The method of claim 1 wherein the angiostatic steroid is present at a concentration of between about 0.005 and 2.0 wt.%.

3. The method of claim 2 wherein the angostatic steroid is administered topically to the eye.

4. The method of claim 1 wherein the angiostatic steroid comprises tetrahydrocortexolone or a pharmaceutically acceptable salt thereof.

5. The method of claim 1 wherein the angiostatic steroid comprises 6α-fluoro-17α,21-dihydroxy-16β-methyl-pregna-4,9(11)-diene-3,20-dione or a pharmaceutically acceptable salt thereof.

6. The method of claim 1 wherein the angiostatic steroid comprises 4,9(11)-pregnadien 17α,21-diol-3,20-dione or a pharmaceutically acceptable salt thereof.

* * * * *